United States Patent

Ishikawa et al.

[11] Patent Number: 5,888,834
[45] Date of Patent: Mar. 30, 1999

[54] IMMUNOASSAY PLATE AND USE THEREOF

[75] Inventors: Eiji Ishikawa, 24-1, Ohtsukadainishi 3-chome, Miyazaki-shi, Miyazaki 880-21; Hidetaka Nakamoto, Takatsuki; Satoshi Tanaka, Ibaraki, all of Japan

[73] Assignees: Sumitomo Pharmaceuticals Company, Limited., Osaka; Eiji Ishikawa, Miyazaki, both of Japan

[21] Appl. No.: 548,128

[22] Filed: Oct. 25, 1995

[30] Foreign Application Priority Data

Oct. 25, 1994 [JP] Japan ..................................... 6-260588
Aug. 31, 1995 [JP] Japan ..................................... 7-223696

[51] Int. Cl.$^6$ .......................... G01N 21/00; G01N 31/22; G01N 33/543
[52] U.S. Cl. .............................. 436/518; 422/57; 422/58; 422/59; 422/62; 422/63; 422/68.1; 422/99; 422/100; 422/101; 422/104; 422/237; 435/7.1; 435/7.5; 435/287.9; 435/961; 436/524; 436/538; 436/541; 436/543; 436/807; 436/810; 436/824
[58] Field of Search .................... 422/57, 58, 59, 422/62, 63, 68.1, 99, 100, 101, 104, 237; 435/7.1, 7.5, 7.92, 7.94, 287.9, 288.2, 288.3, 288.4, 961; 436/518, 524, 538, 541, 543, 807, 809, 810, 824

[56] References Cited

U.S. PATENT DOCUMENTS 3,826,619  7/1974  Bratu et al. .
4,207,289  6/1980  Weiss .
4,225,575  9/1980  Piasio et al. .

(List continued on next page.)

FOREIGN PATENT DOCUMENTS 0 201 339     11/1986  European Pat. Off. .
0 572 217 A1  12/1993  European Pat. Off. .
2 147 698      5/1985  United Kingdom .

82 00058  1/1982  WIPO .

OTHER PUBLICATIONS

Eiji Ishikawa et al., "Development of ultrasensitive enzyme immunoassay reviewed with emphasis on factors which limit the sensitivity", *Molecular and Cellular Probes,* vol. 5, 1991, pp. 81–95.

Setsuko Ishikawa et al., "Simpler and More Sensitive Immune Complex Transfer Enzyme . . . Fluororeader", *Analytical Letter,* vol. 28, No. 9, 1995, pp. 1611–1618.

(List continued on next page.)

*Primary Examiner*—Christopher L. Chin
*Assistant Examiner*—Bao-Thuy L. Nguyen
*Attorney, Agent, or Firm*—Sughrue, Mion, Zinn, Macpeak & Seas, PLLC

[57] ABSTRACT

An immunoassay plate for an immune complex transfer immunoassay, comprising a well type solid phase and a dip stick type solid phase which can be inserted into said well type solid phase, wherein the dip stick type solid phase is coated with either substance (A) or (B) to be mentioned below and the well type solid phase is coated with the other, remaining substance, and these solid phases are used as the two solid phases to be used for an immune complex transfer immunoassay:

(A): a substance having a reactive group which specifically binds to a functional group previously introduced onto a substance, which specifically forms an immune complex with a test substance (B): a substance having a reactive group capable of specifically binding to the test substance in the immune complex, a substance which specifically forms an immune complex with the test substance, or a functional group conjugated in advance with said substance, provided that the moiety which binds to the reactive group of (A) does not bind to the reactive group of (B) and vice versa. According to the present invention, an immune complex transfer immunoassay can be markedly simplified. Consequently, a highly sensitive immune complex transfer immunoassay can be conducted with ease and with high precision.

20 Claims, 7 Drawing Sheets

U.S. PATENT DOCUMENTS

| | | |
|---|---|---|
| 4,271,140 | 6/1981 | Bunting . |
| 4,599,315 | 7/1986 | Terasaki et al. . |
| 4,624,930 | 11/1986 | Tanswell et al. . |
| 4,657,853 | 4/1987 | Freytag et al. . |
| 5,041,266 | 8/1991 | Fox . |
| 5,137,807 | 8/1992 | Yoshida et al. . |
| 5,168,057 | 12/1992 | Oh et al. . |
| 5,236,830 | 8/1993 | Ishikawa . |
| 5,236,849 | 8/1993 | Ishikawa . |
| 5,244,788 | 9/1993 | Hubscher . |
| 5,256,372 | 10/1993 | Brooks et al. . |
| 5,312,730 | 5/1994 | Piran et al. . |

OTHER PUBLICATIONS

Setsuko Ishikawa et al., "Further Simplification of Ultrasensitive Enzyme Immonassay . . . Fluororeader", *Journal of Clinical Laboratory Analysis,* vol. 9, 1995, pp. 204–211.

Eiji Ishikawa et al., "Principle and Applications of Ultrasensitive Enzyme Immunoassay (Immune Complex Transfer Enzyme Immunoassay) for Antibodies in Body Fluids, "*Journal of Clinical Laboratory Analysis,* vol. 7, 1993, pp. 376–393.

F I G. 3(a)
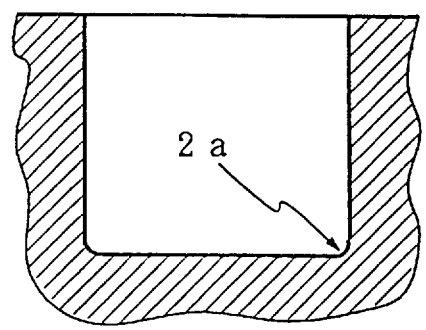
F I G. 3(b)
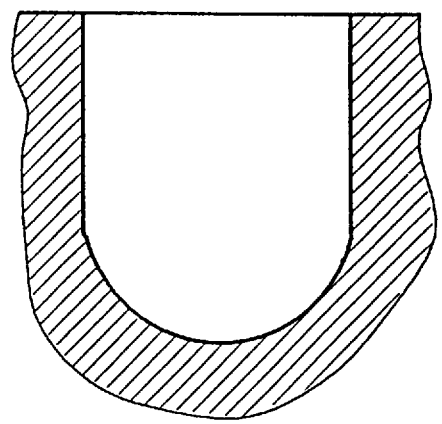

IMMUNOASSAY PLATE AND USE THEREOF

FIELD OF THE INVENTION

The present invention relates to an apparatus useful for the determination of an antigenic substance or an antibody substance by immune complex transfer immunoassay, and immunoassay using this apparatus.

BACKGROUND OF THE INVENTION

An immunoassay is an advantageous method for determining and analyzing an antibody substance or an antigenic substance in that it is simple and has high specificity.

In particular, an immune complex transfer immunoassay is known to suitably suppress adsorption of contaminant protein onto solid phase and thereby-caused occurrence of background signals, which are the defects of sandwich method, and enable high sensitivity assay of an antibody substance or an antigenic substance in a test solution.

As used herein, the antibody substance or antigenic substance to be assayed in a test solution is referred to as test substance.

An immune complex transfer immunoassay is an immunoassay comprising, for example, two cycles of trapping using a pair of solid phases. The operation thereof is schematically explained by referring to an assay of antibody, as an example, from among the test substances. For the explanation's sake, one solid phase from the pair of solid phases, which is used for the first trapping, is referred to as the first solid phase and the other solid phase used for the next trapping is referred to as the second solid phase.

The typical immune complex transfer immunoassay comprises the following steps.

(a) An antigen modified with a functional group and a labeled antigen are bound to a target antibody to form an immune complex having a structure of "functional group-antigen-antibody-antigen-label" as shown, for example, in FIG. 5(a) with a reference number 50.

(b) The immune complex is trapped on a first solid phase via a certain moiety (functional group bound to the antigen in this case) in the immune complex. The immune complex may be trapped after being formed in a test solution or may be completed with respect to one end (functional group) thereof trapped earlier on a solid phase.

(c) The immune complex is released from the first solid phase in a solution used for transferring the immune complex.

(d) The immune complex is trapped on a second solid phase. The moiety of the immune complex which is used for the trapping is different from the moiety used in (b).

(e) The target antibody in the immune complex is assayed using the label conjugated in (a).

More detailed explanation and working examples of immune complex transfer immunoassay are found in the following literature.

(1) ISHIKAWA, E., HASHIDA, S., KOHNO, T., Development of ultrasensitive enzyme immunoassay reviewed with emphasis on factors which limit the sensitivity, MOLECULAR AND CELLULAR PROBES, 5, pp 81–95 (1991)

(2) ISHIKAWA, E., HASHIDA, S., KOHNO, T., et al., Principle and applications of ultrasensitive enzyme immunoassay (Immune complex transfer enzyme immunoassay) for antibodies in body fluids, J. CLIN. LABORATORY ANALYSIS, 7, pp 376–393 (1993)

(3) U.S. Pat. No. 5,236,849 and EP 303229 entitled Method of high sensitivity immunoassay (4) U.S. Pat. No. 5,236,830 and EP 368273 entitled Novel method for assaying antigen (5) ISHIKAWA, Eiji, Ultrasensitive enzyme immunoassay, Gakkai Shuppan Center (1993)

In the conventional immune complex transfer immunoassay, plastic balls called beads having a diameter of about 3 mm are used as the first and the second solid phases. The beads are stirred in a test tube to perform the above-mentioned immune complex transfer immunoassay comprising the steps (a) to (e).

This method requires each one of the beads to be removed from and placed into test tubes with tweezers upon visually discriminating the two kinds of beads, thus raising problems in terms of handling easiness and the possibility of contamination of test tubes caused by carrying immune complex between test tubes with tweezers.

In addition, the possibility of a trace amount of immune complex released from the first solid phase contacting the second solid phase is very low, and only when a substance coated on the second solid phase has high affinity for the binding site of the immune complex, sufficient trapping is accomplished, which in turn results in a tendency that the amount of signals becomes less.

For conventional immunoassay, there have been known assay plates wherein a dip stick type solid phase and a well type solid phase are combined.

U.S. Pat. No. 3,826,619 describes:

(a) a step comprising coating an antibody on a dip stick type solid phase, and dipping the dip stick type solid phase in a test solution in a well type solid phase to trap the assay target, and (b) a step comprising rinsing the dip stick type solid phase, dipping same in a marker solution placed in a different well type solid phase and assaying the assay target.

The dip stick type solid phase used in these steps functions merely as a means for trapping the assay target, and the well type solid phase is nothing but a container to keep a solution.

Japanese Patent Application under WO 82/00058 teaches a special one step sandwich immunoassay using the above-mentioned assay plate wherein the dip stick type solid phase and the well type solid phase are combined, which comprises:

(a) coating a sustained release marker dissolved in a sucrose solution and the like on a well type solid phase, (b) placing a test solution in the well type solid phase, and (c) dipping an antigen-bound dip stick type solid phase in said test solution, thereby trapping the assay target antibody and simultaneously binding the marker.

This method rather resembles the method using the immunoassay plate of the present invention in that it uses a well type solid phase and a dip stick type solid phase in combination. However, the well type solid phase only functions as a marker carrier, and to improve assay target-marking performance.

In contrast to the immunoassay using conventional plates, an immune complex transfer immunoassay comprises a specific process of transferring an immune complex containing a trace amount of an assay target from the first solid phase to the second solid phase, but an immunoassay apparatus capable of sufficiently accomplishing the transfer process has not been known.

Hence, there has been a demand for the development of an immunoassay apparatus capable of performing immune complex transfer immunoassay with ease and at high sensitivity, which can be suitably applied to clinical tests.

SUMMARY OF THE INVENTION

It is therefore an object of the present invention to provide a highly sensitive immunoassay plate for immune complex transfer immunoassay, which is easy to handle, obviates contamination which may be caused by the use of plural test tubes, enables efficient and sufficient transfer of an immune complex from the first solid phase to the second solid phase (which being the point of immune complex transfer immunoassay), and allows automation of the procedures, and use thereof.

The present invention provides the following.

(1) An immunoassay plate for immune complex transfer immunoassay, comprising a well type solid phase and a dip stick type solid phase which can be inserted into said well type solid phase, wherein the dip stick type solid phase is coated with one of substance (A) and substance (B) to be mentioned below and the well type solid phase is coated with the other substance, and these solid phases are used as the two solid phases to be used for an immune complex transfer immunoassay:

(A): a substance having a reactive group which specifically binds to a functional group previously introduced onto a substance which specifically forms an immune complex with a test substance (B): a substance having a reactive group capable of specifically binding to the test substance in the immune complex, a substance which specifically forms an immune complex with the test substance, or a functional group previously introduced onto said substance, provided that the moiety which binds to the reactive group of (A) does not bind to the reactive group of (B) and vice versa.

(2) The immunoassay plate of (1) above, wherein the substance (A) is adhered to the surface of the dip stick type solid phase and the substance (B) is adhered to the surface of the well type solid phase, which plate being used for the assay of an antibody.

(3) The immunoassay plate of (1) or (2) above, wherein the distance between the dip stick type solid phase and the well type solid phase, when the two phases are combined by inserting the dip stick type solid phase into the well type solid phase, is not more than 1 mm at the shortest in not less than 50% of the immune complex binding surface of the dip stick type solid phase.

(4) The immunoassay plate of (1) or (2) above, wherein the dip stick type solid phase and/or the well type solid phase are/is applied with a surface treatment to increase the amount of adsorbed protein.

(5) The immunoassay plate of (1) or (2) above, wherein the material of the dip stick type solid phase and/or the well type solid phase is polystyrene.

(6) The immunoassay plate of (1) or (2) above, wherein the functional group which is introduced onto the substance which specifically forms the immune complex with the test substance and binds to the substance (A) is a hapten, and the substance (A) is an anti-hapten antibody, which is anti-DNP (dinitrophenyl) antibody, anti-MNP (mononitrophenyl) antibody or anti-TNP (trinitrophenyl) antibody.

(7) The immunoassay plate of any one of (1) to (6) above, wherein the shape of the dip stick type solid phase where an immune complex binding surface has been formed is columnar with a conical end pointed toward the end thereof.

(8) The immunoassay plate of any one of (1) to (7) above, wherein the dip stick type solid phase has a constriction capable of inhibiting capillarity of a solution for transfer reaction (hereinafter referred to as transfer solution), which occurs between the dip stick type solid phase and the well type solid phase, at some point near the root and opposite from the portion to be dipped in a transfer solution to be reacted.

(9) The immunoassay plate of any one of (1) to (8) above, wherein the shape of the dip stick type solid phase and the well type solid phase where an immune complex binding surface has been formed is columnar with one or more protrusions having a height of not more than 1 mm formed on the body of the immune complex binding surface on the columnar dip stick type solid phase.

(10) The immunoassay plate of (9) above, wherein the protrusion protrudes toward the peripheral direction from the body of the columnar portion and has a ridge line extending along the longitudinal direction of the body of the columnar portion.

(11) The immunoassay plate of any one of (1) to (10) above, wherein plural well type solid phases are set in a predetermined arrangement on a plate and the dip stick type solid phases are set on a different plate in the same arrangement with the well type solid phases.

(12) The immunoassay plate of (9) or (10) above, wherein at least three well type solid phases are set in a predetermined arrangement on a plate; dip stick type solid phases are set on a different plate in the same arrangement with the well type solid phases; each dip stick type solid phase having one protrusion; and at least one protrusion is formed at every position determined for setting a protrusion, which position being defined in (C) below:

(C): at least three positions determined on the periphery of the body of the dip stick type solid phase, wherein the distance between the positions is that which prevents the body of the dip stick type solid phase from contacting the well type solid phase when protrusions are formed at all of these positions.

(13) The immunoassay plate of (12) above, wherein four positions are determined according to (C), and the distance between these four positions is the same.

(14) The immunoassay plate of any one of (11) to (13) above, comprising at least one plate for keeping a solution necessary for reaction, which plate comprising wells having the same shape with the well type solid phase that are set in the same number and in the same arrangement as said well type solid phase, the dip stick type solid phase and the well type solid phase as one set.

The method for immune complex transfer immunoassay of the present invention comprises the use of the above-mentioned immunoassay plates (1)–(14), and is characterized by trapping an immune complex in the test solution on either the dip stick type solid phase or the well type solid phase, inserting the dip stick type solid phase into the well type solid phase, releasing the immune complex in the liquid phase in the well type solid phase, trapping this immune complex on the remaining well type solid phase or dip stick type solid phase, and assaying an antigen or antibody in the immune complex by assaying a label.

BRIEF DESCRIPTION OF THE DRAWINGS

FIGS. 3(a) and (b) show an example of the well type solid phase used in the present invention.

DETAILED DESCRIPTION OF THE INVENTION

Figure 1:
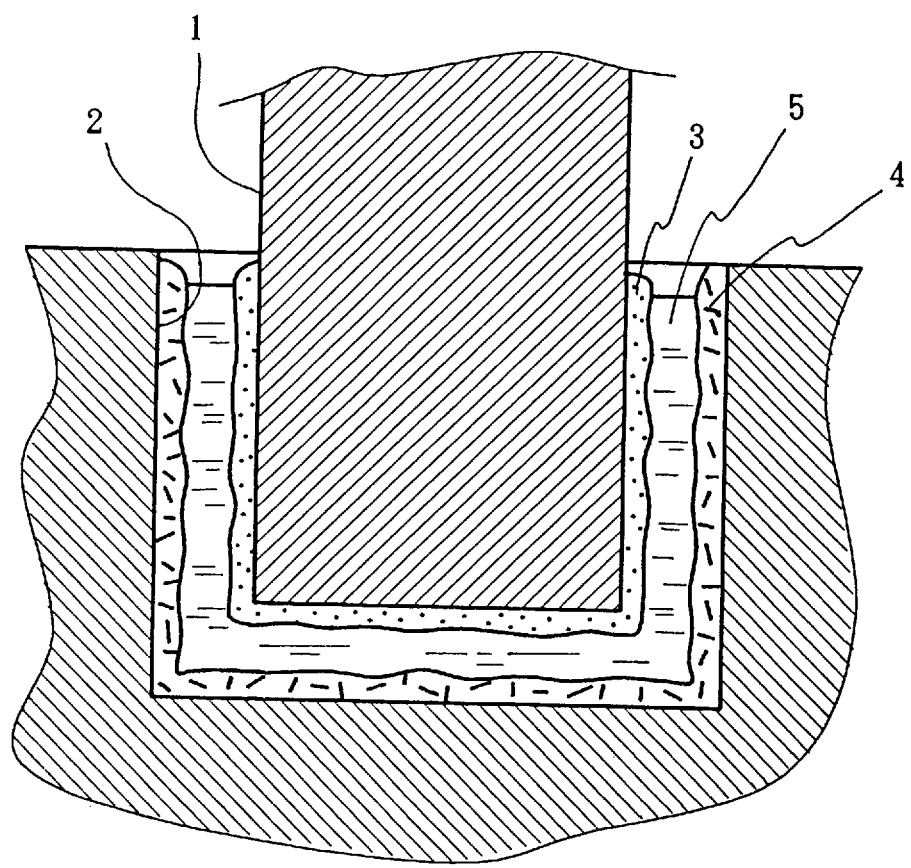
FIG. 1 is a schematic cross sectional view of the basic structure of the immunoassay plate of the present invention.

In the present specification, the substance of the above-mentioned (A) is to be referred to as "receptor substance A" and the substance of (B) is to be referred to as "receptor substance B".

As used herein, the dip stick type solid phase is a convex solid phase having a shape allowing insertion into the well type solid phase to be mentioned later, and is used for dipping in a solution contained in a well type solid phase.

The well type solid phase is a concave solid phase having a shape allowing insertion of the dip stick type solid phase mentioned above, and is used for keeping a test solution, transfer solution to be reacted, a reaction solution for detecting enzyme marker and the like.

By the immune complex binding surface is meant a region which traps an immune complex when the receptor substance A or B is adhered by coating and the like to a surface of the well type solid phase or a surface of the dip stick type solid phase, and these two solid phases in combination are brought into contact with a test solution or a transfer solution to be reacted.

The following effects which have been conventionally unattainable can be provided by the present invention which comprises adhering, by coating etc., receptor substances for trapping an immune complex at different surfaces, to the surface of the dip stick type solid phase and the well type solid phase, and using them as a pair of solid phases for immune complex transfer immunoassay.

(a) Two kinds of solid phases can be easily brought extremely close to each other or separated and plural assays can be performed at the same time.

(b) Using a well type solid phase as one of the two phases, the function of a carrier which traps the immune complex and the function of keeping the transfer solution can be fulfilled simultaneously.

(c) The entirety of the immune complex binding surface of the first solid phase and that of the second solid phase can be faced with each other. The distance between the two immune complex binding surfaces can be optionally changed, so that they can face with each other at an extremely small distance.

The above-mentioned effects (a) to (c) resolve the problems peculiar to the immune complex transfer immunoassay, i.e., they simplify the complicated steps absent in conventional immunoassay but required in conventional immune complex transfer immunoassay, and improve efficiency of the immune complex transfer immunoassay.

To be specific, the immunoassay plate of the present invention has eliminated insertion or removing of beads with tweezers which have been done in conventional transfer methods. It also simplified manipulation by obviating the step of discriminating the two beads used as the first phase or the second phase, which are similar in appearance (which discriminating having been a difficulty in the immune complex transfer immunoassay) by employing the completely different shape of the dip stick type solid phase and the well type solid phase.

In the immunoassay plate of the present invention, the well type solid phase serves both as a solid phase and a container as mentioned in (b). As a result, the number of the independent solid phase present in a transfer solution is two (first solid phase and second solid phase) in contrast to three kinds of solid phases (first solid phase, second solid phase and inner wall of the container carrying them), thus contributing to an improved sensitivity of the assay.

In conventional immune complex transfer immunoassay, the two kinds of beads used as the first and the second solid phases face each other and come close to each other only in a limited area, and the rest of the spherical surfaces respectively face opposite directions. In the conventional methods using such beads, an immune complex is released from the first solid phase into a transfer solution and freely diffused therein. For more amount of the immune complex to be trapped on the second solid phase, there is no other way but to thoroughly stir the transfer solution for a long time with a mechanical aid to increase the probability of trapping.

In contrast, the immunoassay plate of the present invention enables the immune complex binding surface of the second solid phase to face the immune complex binding surface of the first solid phase, up to 100% where necessary, as mentioned under (c), which ultimately increases the probability of the immune complex released from the first solid phase encountering the second solid phase.

In particular, free diffusion of the immune complex after release can be greatly reduced and the immune complex trapped on the first solid phase can be linearly and quickly transferred to the second solid phase via an extremely thin layer of the transfer solution, by sufficiently closing the first and the second solid phases to the extent that the distance between them is not more than 1 mm. Moreover, the present invention is advantageous in that the surface area of the solid phase, with which the transfer solution contacts, increases when the same amount of the transfer solution is filled, as compared with other construction wherein the distance is greater. In this way, the transfer efficiency of the immune complex can be enhanced.

The present invention is explained in more detail by way of illustrative Figures.

FIG. 1 is a schematic cross sectional view of the basic structure of the immunoassay plate of the present invention. In this FIG., 1 is a dip stick type solid phase to which a receptor substance 3 is adhered on the surface. 2 is a well type solid phase to which a receptor substance 4 is adhered on the surface. 5 is an immune complex transfer solution to be reacted, which is contained in a well type solid phase. Note that the receptor substance 3 is either the aforementioned receptor substance A or B and the receptor substance 4 is the other receptor substance.

These solid phases are formed in such a shape that enables insertion of the dip stick type solid phase into the well type solid phase to combine them, wherein the dip stick type solid phase is used as either the first solid phase or the second solid phase for immune complex transfer immunoassay, and the well type solid phase is used as the other solid phase.

The dip stick type solid phase and the well type solid phase are explained in terms of material and shape in the following.

The material for the dip stick type solid phase and the well type solid phase may be any as long as it can serve as a solid carrier for trapping the immune complex. Preferred are plastic and glass from the aspects of resistance to chemicals and processability, with particular preference given to polystyrene, nylon and cellulose acetate.

Alternatively, the end portion of the dip stick type solid phase and rod body thereof may be formed from different materials to enhance the reactivity of the end portion and optionally adjust the strength of the body.

The shape of the dip stick type solid phase and the well type solid phase may be such that it allows the dip stick type solid phase to be inserted into the well type solid phase.

The cross section perpendicular to the longitudinal direction (the direction of depth) of the dip stick type solid phase and the well type solid phase may be round, polygon or undefined shape. Preferred is a round cross section from the aspects of manufacture, reaction and washing.

The shape of the tip of the dip stick type solid phase and the bottom of the well type solid phase is typically plane, pyramid or hemisphere. When they are hemisphere, the dip stick type solid phase is a convex hemisphere and the well type solid phase is a concave hemisphere. The convex tip of the dip stick type solid phase is preferably a downwardly protruding convex so that air foams are not formed during insertion.

Figure 2A:
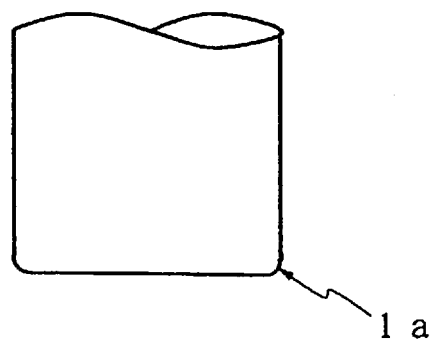
FIGS. 2(a)–(c) show an example of the dip stick type solid phase used in the present invention.
Figure 2B:
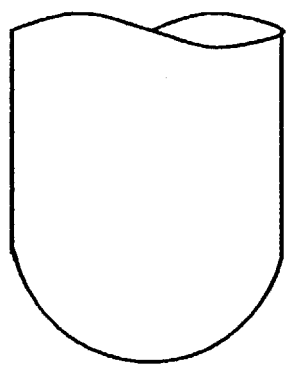
Figure 2C:
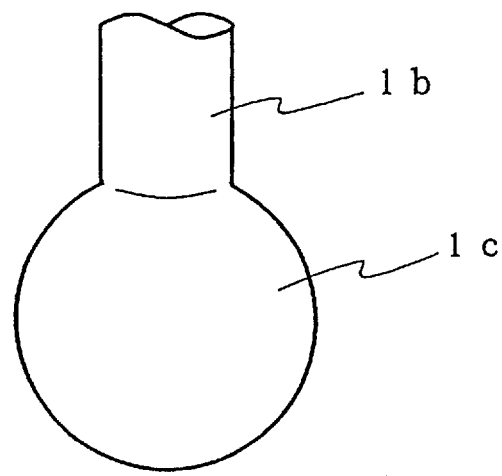

FIG. 2 shows an exemplary shape of the dip stick type solid phase used in the present invention. FIG. 2(a) shows a columnar shape with a flat end surface. Note that a corner edge 1a may be chamferred or curved according to the object of use. FIG. 2(b) shows a columnar shape with a convex hemisphere end. FIG. 2(c) shows a combination of a sphere 1c and a column 1b.

FIG. 3 shows an example of the well type solid phase. FIGS. 3(a) and 3(b) are both tubular holes, wherein the bottom surface is planar in FIG. 3(a) and concave hemisphere in FIG. 3(b). A bottom corner 2a in FIG. 3(a) may be curved in line with the shape of the corner edge of the dip stick type solid phase.

Preferable combinations of the dip stick type solid phase and the well type solid phase are that of FIG. 2(a) and FIG. 3(a), and FIG. 2(b) and FIG. 3(b), in consideration of the fact that the entire immune complex binding surfaces on both phases can face each other and the distance between the phases can be made constant. In particular, greater amount of released immune complex can be trapped by specifically determining the diameter of the dip stick type solid phase and the inner diameter of the well type solid phase in such a way that the distance between the two phases is not more than 1 mm in 50% or more of the immune complex binding surface of the both solid phases, preferably in the entirety thereof, which leads to higher assay sensitivity than conventional assays using two beads.

The bottom surface of the well type solid phase is advantageously planar, since focal distance can be easily set in optical determinations.

The more preferable combination of the dip stick type solid phase and the well type solid phase is as follows.

As mentioned above, the preferable bottom shape of the well type solid phase is planar, and the preferable combination of the dip stick type solid phase and the well type solid phase is FIG. 2(a) and FIG. 3(a), namely, the combination of columnar solid phases.

Figure 6:
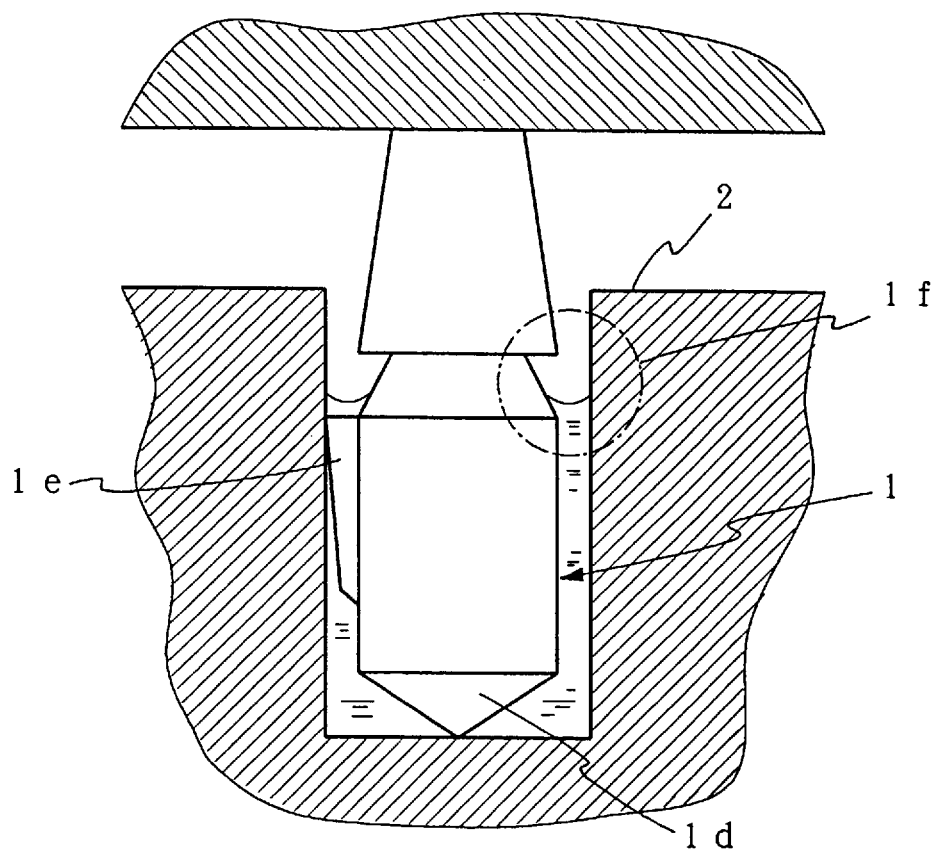
FIG. 6 shows a preferable example of the dip stick type solid phase.

In this case, the shape of the tip 1d of the dip stick type solid phase is preferably a cone pointedly formed from the end of the columnar portion of the dip stick type solid phase, as shown in FIG. 6. The angle of the tip of the cone is preferably an obtuse angle of about 100–150 degrees. Such shape makes air bubbles less dwelling below the dip stick type solid phase, when the dip stick type solid phase and the well type solid phase are drawn closer to each other.

The distance between the dip stick type solid phase and the well type solid phase is preferably not more than 1 mm as mentioned above. When a transfer solution is present between these solid phases during immune complex transfer immunoassay, the liquid surface of the transfer solution is not stable but becomes nonuniform due to the capillarity between these solid phases.

A preferable mode for reducing such problem is shown in FIG. 6. That is, a constriction 1f is formed on the body of the dip stick type solid phase 1 to prevent capillarity by preventing the transfer solution from rising above the constriction. Such a constriction or ditch can be made on the surface of the well type solid phase.

The depth of the constriction is the same as the gap needed to prevent capillarity between the solid phases.

The shape of the constriction may be any as long as the capillarity can be inhibited thereby. The preferable shape is shown in FIG. 6 wherein the portion of the constriction near the root of the dip stick type solid phase loses radius to a desired extent toward the direction perpendicular to the longitudinal direction of the solid phase and gradually gains radius as it proceeds toward the tip thereof, for the reasons of easy manufacture.

The presence of such constriction stops the rise of the transfer solution due to capillarity and inhibits expansion of nonuniform solution surface, so that uniform and efficient assay can be achieved and an increase in background can be prevented.

The immune complex binding surface of the dip stick type solid phase preferably has one or more protrusions having a height of not more than 1 mm. The protrusions obviate contact between the immune complex binding surface of the dip stick type solid phase and the immune complex binding surface of the well type solid phase. Such protrusions can be made on the surface of the well type solid phase.

The shape of the protrusions may be any as long as they stick out from the body, such as cone, pyramid, truncated cone and truncated pyramid.

The preferable shape of the protrusion is shown in FIG. 6 with a reference symbol 1e, wherein a triangular or trapezoidal protrusion is formed on the periphery of the columnar body and the protrusion draws a ridge line along the longitudinal direction of the columnar body.

The ridge line along the longitudinal direction is preferably such that the height of the protrusion decreases toward the tip, so that the dip stick type solid phase can be easily inserted into the well type solid phase, as shown in FIG. 6.

When only one pair of the dip stick type solid phase and the well type solid phase is present, three or more protrusions are preferably formed in the peripheral direction of the body of the dip stick type solid phase. In this case, the distance between the protrusions is preferably that which prevents contact between the body of the dip stick type solid phase and the well type solid phase, with particular preference given to the distance between the protrusions on the periphery being identical.

The above-mentioned mode is markedly useful in the immune complex transfer immunoassay wherein the use of the dip stick type solid phase and the well type solid phase located nearby is particularly important. The dip stick type solid phase can be inserted into the well type solid phase while maintaining the longitudinal central axis of the dip stick type solid phase sufficiently close to the longitudinal central axis of the well type solid phase, whereby the distance between the immune complex binding surface of both solid phases can be constantly kept at a certain level to accomplish a uniform and efficient assay.

It is preferable that the surface of the dip stick type solid phase and the well type solid phase have appropriate roughness to enhance adsorption of the immune complex. The method for treating the surface includes various mechanical abrasions and chemical corrosion treatments.

Figure 4A:
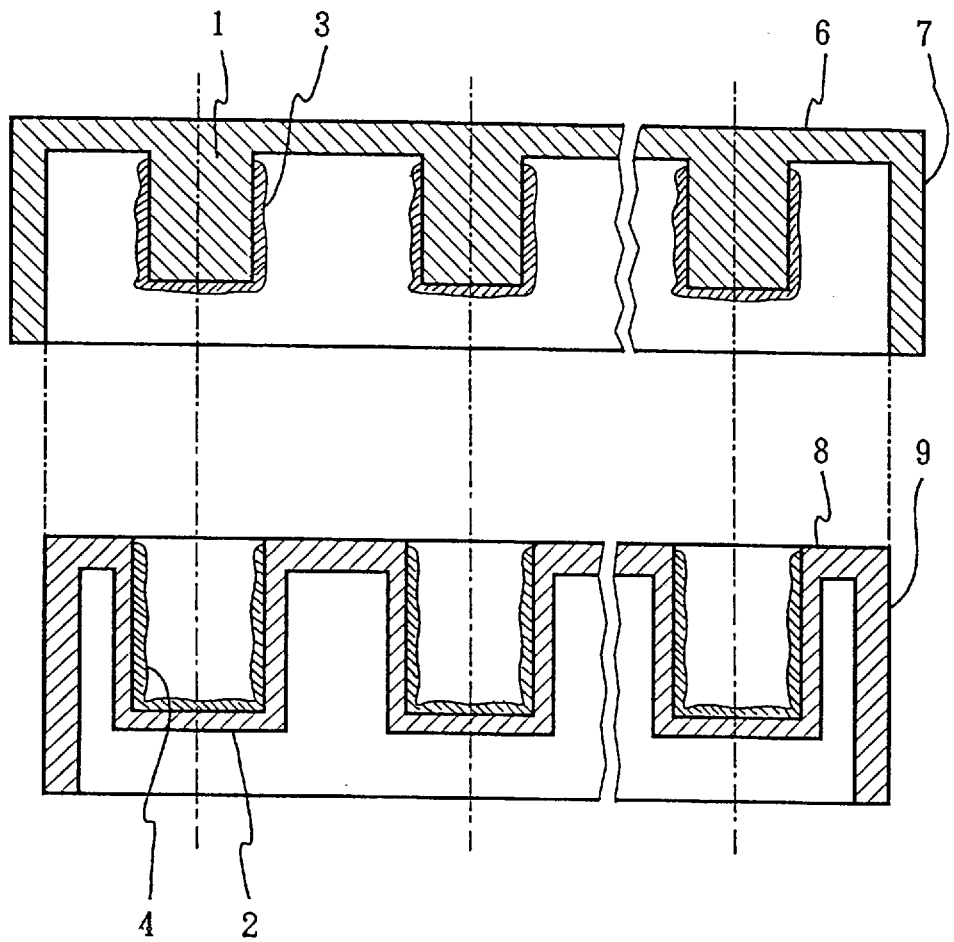
FIGS. 4(a) and (b) are schematic showings of a preferable example of the present invention.

When a dip stick type solid phase is inserted into a well type solid phase, an insertion guide is preferably formed to enable insertion wherein respective longitudinal central axes are coincided. For example, a structure comprising a pilot pin and a hole, a key and a groove and the like is preferable. A specific example is shown in FIG. 4(a) wherein the outside of the entire periphery 9 of one of the well type solid phase and the dip stick type solid phase (well type solid phase in FIG. 4(a)) is regarded as a pilot pin, and the inside of the entire periphery 7 of the other solid phase (dip stick type solid phase in FIG. 4(a)) is regarded as a hole for positional determination.

One of the preferable modes of the immunoassay plate of the present invention comprises simultaneous use of plural combinations of the dip stick type solid phase and the well type solid phase.

FIG. 4 is a schematic showing of a preferable example of the immunoassay plate of the present invention. In the Figure, plural dip stick type solid phases 1 are arranged on a substrate 6 in a predetermined manner, the same number of well type solid phases 2 are arranged on a different substrate 8 in the same arrangement, and plural transfer tests can be simultaneously performed by combining them.

While the above-mentioned arrangement is not limited, the arrangement preferably has a constant pitch. An advantage can be obtained when the arrangement is the same as that of commercially available plural well microplates which are used in the field of biochemical studies, since it enables use of associated equipments for measurements.

As mentioned above, when plural pairs of a dip stick type solid phase and a well type solid phase are simultaneously used, the protrusions to be formed on the dip stick type solid phase are dispersed thereon to reduce the number of protrusions formed on respective dip stick type solid phases. For example, when two pairs of a dip stick type solid phase and a well type solid phase are used instead of one dip stick type solid phase having four protrusions, the four protrusions may be dispersed on the two dip stick type solid phases by two. The protrusions may be dispersed by forming one protrusion on one solid phase and three protrusions on the other solid phase. When the four protrusions as a whole cover the original four points to be covered by the four protrusions, the effect of the protrusions will be the same as that achieved when one dip stick type solid phase has four protrusions.

When three or more pairs of a dip stick type solid phase and a well type solid phase are used, in particular, it is preferable that only one protrusion be formed on one dip stick type solid phase. It should be noted that at least one protrusion is formed at every position set for forming protrusions according to (C) mentioned above. As explained supra, when at least one protrusion is formed at the three positions, the effect of the protrusions will be the same as that obtained when one dip stick type solid phase has three protrusions, even if only one protrusion is formed on one dip stick type solid phase.

In this way, insertion of the dip stick type solid phase can be made possible while maintaining the longitudinal central axis thereof sufficiently nearing the longitudinal central axis of the well type solid phase. As a result, the distance between the immune complex binding surfaces of the both solid phases can be constantly kept at a certain level to accomplish a uniform and efficient assay.

The protrusion formed on respective dip stick type solid phase being one, the contact point with the well type solid phase becomes less, and rinsing of the solid phase can be beneficially facilitated.

A preferable example of the position of (C) mentioned above is four positions in the peripheral direction of the body of the dip stick type solid phase, the distance between the protrusions being the same. When seen from a cross section perpendicular to the axis of the body of the dip stick type solid phase, the protrusions are formed at four sites at equal 90 degree intervals around the axis on the periphery of the body.

Figure 7A:
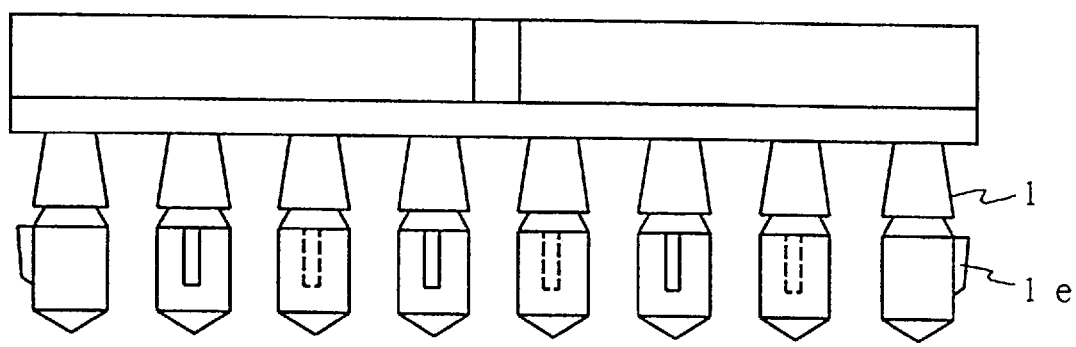
FIGS. 7(a) and (b) show a preferable embodiment wherein plural dip stick type solid phases are used.
Figure 7B:
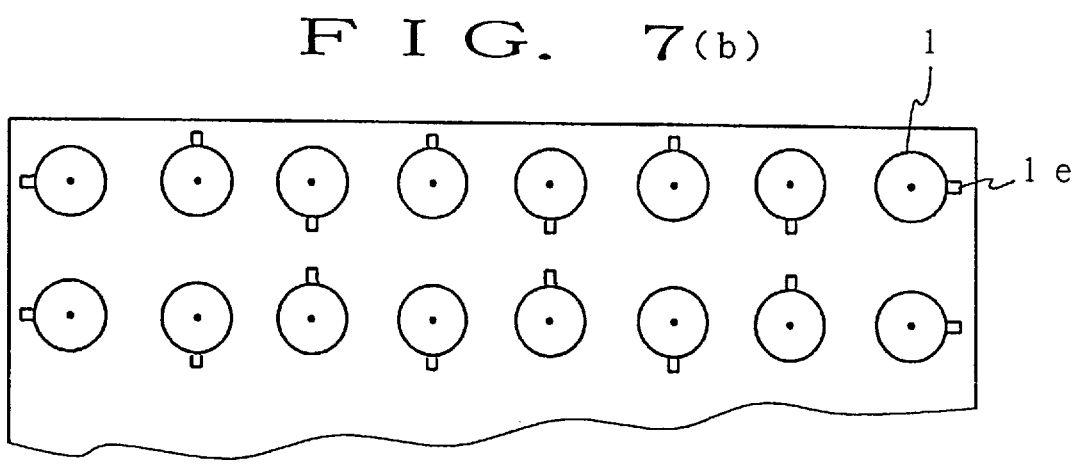

FIG. 7 schematically shows a specific embodiment of this mode. The dip stick type solid phases 1 shown in FIG. 7(a) (side view) are formed at 96 sites on a substrate (8 sites a row×12 rows) to correspond to a well type solid phase formed as a standard matrix arrangement of 96 wells (8 wells a row×12 rows). FIG. 7(b) is a view of the dip stick type solid phases shown in FIG. 7(a), which are seen from the end of the solid phase.

The respective dip stick type solid phases shown in FIG. 7(a) are formed in the same manner as in FIG. 6. The important characteristic thereof is the location of a protrusion 1e. As shown in FIG. 7(b), the protrusion 1e is arranged in such a manner that it faces either of the four directions set on the periphery of the body of each dip stick type solid phase. Moreover, at least one protrusion is formed in the four directions. That is, the protrusion of respective dip stick type solid phase is arranged so that there is no direction which is not covered by a protrusion. In FIG. 7(b), for example, all four positions are covered by respective protrusions of 16 dip stick type solid phases in the adjacent two rows.

The combination of the number of the dip stick type solid phase and the position of the above-mentioned (C) for forming protrusions is optionally determined. When the number of the dip stick type solid phase is three, there are set three positions, with all protrusions on the respective dip stick type solid phases facing different directions. When the number of the dip stick type solid phase is four or more, the positions of the above-mentioned (C) can be optionally increased in number such as not less than three. In view of the balance between the actual manufacture costs and the above-mentioned effects provided by the protrusions, however, the number of the positions (C) is preferably about four.

Another preferable embodiment of the immunoassay plate of the present invention comprises the above-mentioned combination of the dip stick type solid phase and the well type solid phase, and one or more wells as containers for keeping the solution necessary for the reaction, thus using the well(s) and the combination of the dip stick type solid phase and the well type solid phase as one set.

The number of the additional wells to be used can be determined according to the object of use, and the wells are used, for example, for keeping the test solution to be used in the first step of the immune complex transfer immunoassay or as accessory containers to be used in the last step of the immune complex transfer immunoassay.

Figure 4B:
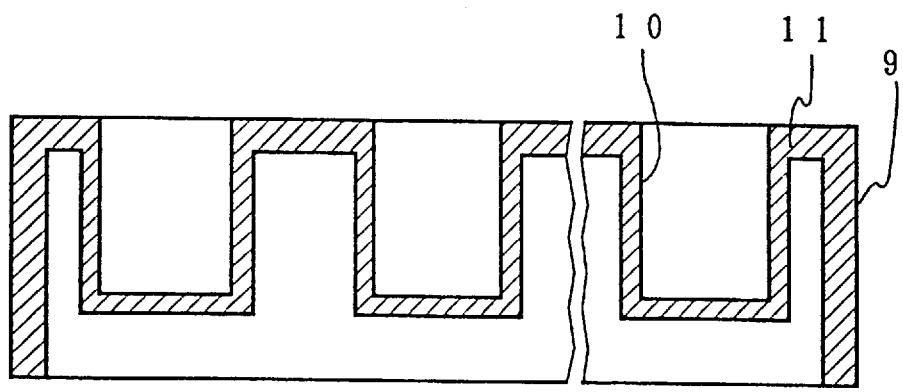

As shown in FIG. 4(b), a well 10 having the same shape as the well type solid phase is preferably installed on a substrate 11 in the same number and in the same arrangement as said well type solid phase and provided with a guide 9 having the same structure with the guide of the well type solid phase.

In this embodiment, a preliminary step or a post-step can be successively done before or after the step of dipping the dip stick type solid phase in a transfer solution in the well type solid phase, which in turn leads to easier and more accurate steps for immune complex transfer immunoassay.

Whether the dip stick type solid phase or the well type solid phase is used as the first solid phase, the receptor substance to be adhered to the surface of the first solid phase is the above-mentioned receptor substance A and that to be adhered to the surface of the second solid phase is the above-mentioned receptor substance B.

In the following, the receptor substances A and B are described in more detail along with the description of the immune complex transfer immunoassay using the immunoassay plate of the present invention.

One embodiment of the immune complex transfer immunoassay using the immunoassay plate of the present invention, in which an antibody substance is the test substance, is explained in the following. While the first solid phase may be a dip stick type solid phase or a well type solid phase, a dip stick type solid phase is used as the first solid phase in the following example.

As schematically shown in FIG. 5, the steps for antibody assay by the immune complex transfer immunoassay using the immunoassay plate of the present invention comprise the following (a), (b) and (c).

(a) An antibody 20 to be assayed is bound with an antigen 30 bound with a functional group 31, and an antigen 40 bound with a label 41 in a test solution 12 to form an immune complex 50. The test solution 12 is preferably kept in a well having the same shape as the well type solid phase. The immune complex 50 is trapped on a dip stick type solid phase 1 via the functional group 31. A receptor substance 3 coated on the dip stick type solid phase 1 is the above-mentioned receptor substance A which has a reactive group specifically binding to the functional group 31.

(b) The dip stick type solid phase is rinsed to leave only the trapped immune complexes. The dip stick type solid phase 1 is inserted into a well type solid phase 2 to release the immune complexes in a transfer solution 5, which is kept in said well type solid phase. The released immune complexes are trapped on the well type solid phase 2 via the antibody 20. A receptor substance 4 coated on the well type solid phase 2 is a receptor substance B specifically binding to the antibody 20. This substance may be a substance having a reactive group capable of specifically binding to a functional group different from the functional group 31 bound with the antigen 30. Note that this functional group should not bind to the reactive group of the substance of (A).

(c) The antibody in the immune complexes trapped on the well type solid phase 2 is assayed according to the label 41. The assay method using a label may be a known method.

Examples of the test solution include body fluids such as serum, plasma, cerebrospinal fluid, saliva and urine, and buffer containing antibody.

The antibody to be assayed includes all antibodies substantially assayable by immunological methods. Examples thereof include autoantibodies such as antinuclear antibody, anti-DNA antibody, anti-RNA antibody, rheumatoid factor, anti-erythrocyte antibody, anti-mitochondria antibody, anti-muscle antibody, antithyroid antibody (e.g. anti-microsome antibody, anti-thyroglobulin antibody and anti-TSH receptor antibody), anti-insulin antibody, anti-insulin receptor antibody and anti-acetylcholine receptor antibody, antibody against virus or microorganism, antibody against protein preparations (e.g. interferon and human growth hormone) and allergen antibody of allergic diseases. These antibodies can be assayed not only when they are released in a test solution but also when bound to an immune complex or a binding protein.

When an antigen is to be assayed, the assayable antigen includes all substances having an antigenic determinant and substantially all substances capable of being assayed by a conventional immunological assay. Examples thereof include enzymes such as γ-glutamyltranspeptidase (γ-GTP), alkaline phosphatase and glycosyltransferase, protein hormones such as thyroid-stimulating hormone (TSH), luteinizing hormone (LH), human chorionic gonadtropin (hCG), insulin, secretin and growth hormone (GH), plasma proteins such as fibrin degradation product (FDP), C-reactive protein (CRP), $\alpha_1$-acid glycoprotein ($\alpha_1$-AGP), $\alpha_1$-antitripsin ($\alpha_1$-AT), $\alpha_2$-plasmin inhibitor ($\alpha_2$-PI), $\beta_2$-microglobulin ($\beta_2$-MG) and immunoglobulin, carcinoembryonic proteins such as α-fetoprotein (AFP), carcinoembryonic antigen (CEA) and embryonal ferritin, cells such as lymphocyte and microorganism, virus particle, cell surface antigen, and haptens such as thyroxine, vasopressin and atrial natriuretic hormone. These antigens can be assayed not only when they are released in a test solution but also when bound to an immune complex or a binding protein.

Figure 5A:
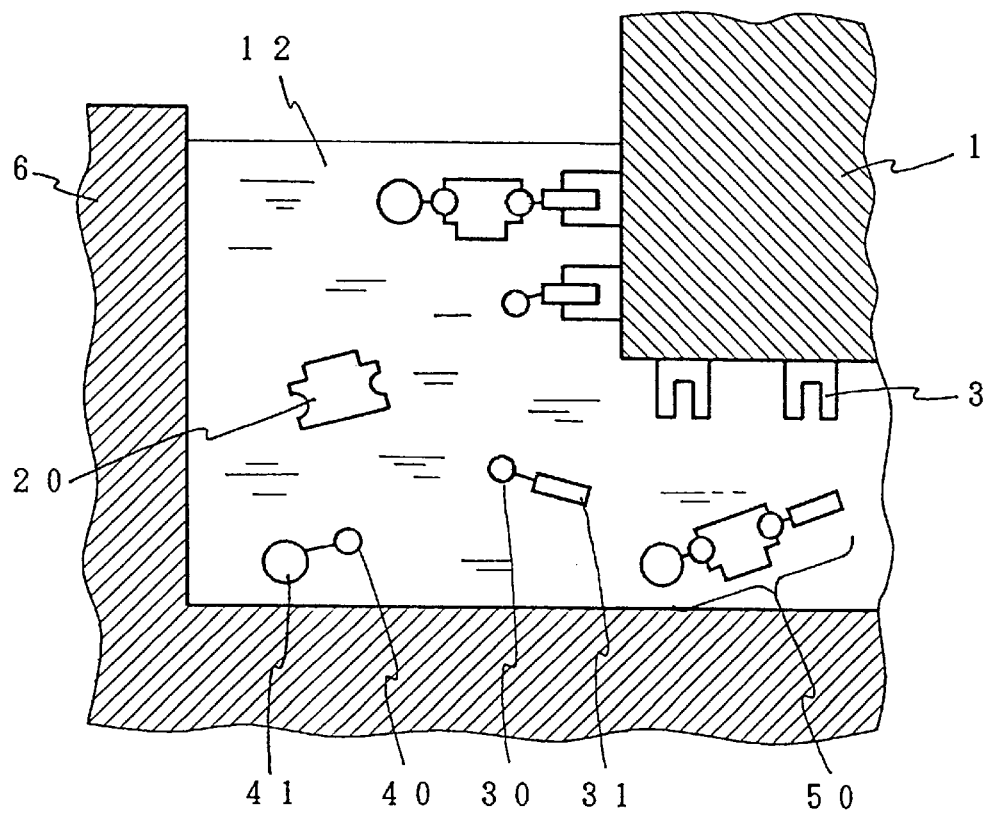
FIGS. 5(a) and (b) are schematic showings of one embodiment of the antibody assay by immune complex transfer immunoassay using the immunoassay plate of the present invention.
Figure 5B:
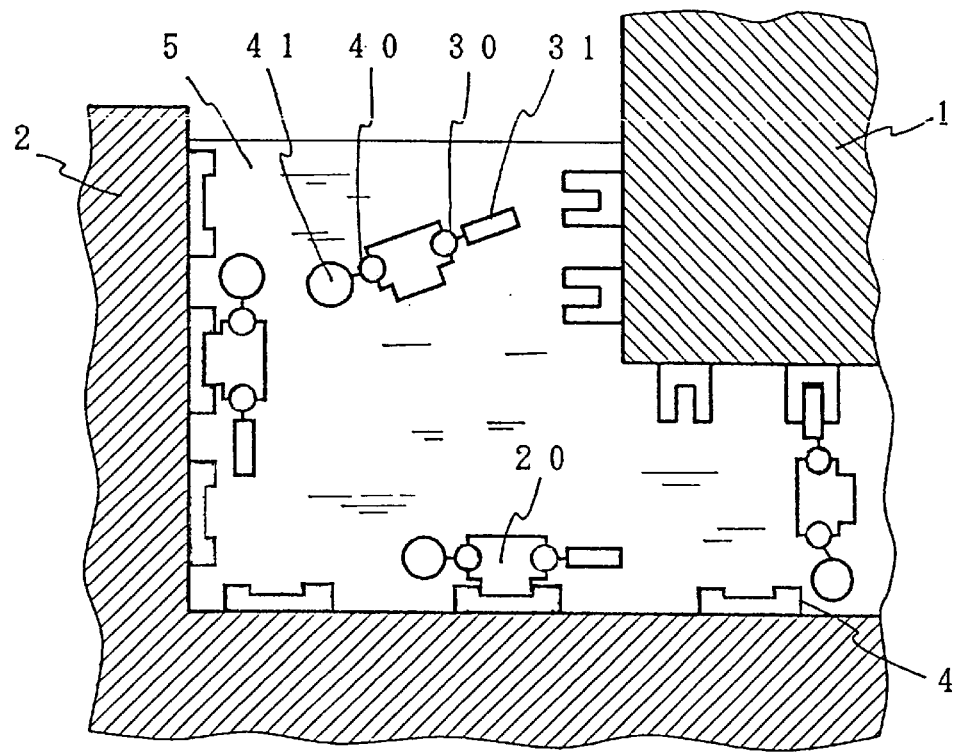

The antigens 30 and 40 shown in FIG. 5(b) are components which cause an antigen-antibody reaction with an antibody to be assayed, such as specific antigen and anti-idiotype antibody. In immune complex transfer immunoassay, an antigen preferably does not allow concurrent binding thereto of a functional group and a label.

The functional group to be bound to the aforementioned antigen is involved in trapping on a dip stick type solid phase, and preferably shows binding property which is free of being inhibited by other components in the test solution and being released by rinsing after trapping.

Examples of such functional group include haptens such as dinitrophenyl group, mononitrophenyl group, trinitrophenyl group and fluorescein group, biotin, and antibodies and antigens other than the antibody and antigen constituting the immune complex.

The substance to be used as a label may be any which is usable in immunological assays, and is exemplified by enzyme, radioactive substance, luminescent substance, fluorescent substance and metallic compounds. The enzyme includes, for example, peroxydase, β-D-galactosidase and alkaline phosphatase, the radioactive substance includes, for example, iodine-125 and tritium, fluorescent substance includes, for example, fluorescein isothiocyanate and luminescent substance includes, for example, acridium salt.

A functional group and a label are bound to an antigen by a method known per se, and a carrier which does not affect the steps of immune complex transfer immunoassay may be used to bind them to an antigen. Binding in this manner is particularly preferable when the antigen has a low molecular weight. Examples of the carrier include nonspecific rabbit IgG, bovine serum albumin and dextran.

The receptor substance to be adhered to the dip stick type solid phase is the aforementioned receptor substance A, i.e. the substance 3 in FIG. 5(a) which is capable of specifically binding to the functional group 31.

Such receptor substance is exemplified by those reactive with functional group. When the functional group is hapten, for example, a specific antibody against hapten (i.e. anti-hapten antibody) can be used. Specific examples include anti-dinitrophenyl antibody, anti-mononitrophenyl antibody and anti-trinitrophenyl antibody. When the functional group is biotin, avidin and streptoavidin are exemplified. When the functional group is antigen or antibody, an antibody or an antigen against same can be used.

The receptor substance can be adhered to the surface of the dip stick type solid phase by a known method for preparing a carrier in immunological assay.

As the transfer solution to be kept in a well type solid phase, a solution which releases immune complex trapped on a dip stick type solid phase or a solution added with a substance imparting such property is used.

When immune complex is released by treating with an acid, an alkali, a high concentration inorganic salt and the like, the pH is not more than 5, preferably 0.5–3.5, for releasing with an acid; and not less than 9 for releasing with an alkali. In the case of liberation with a high concentration inorganic salt, the concentration of the salt is not less than 2M. These treatments are generally performed at 0°–45° C. for 10 minutes to several dozen hours.

The immune complex is released by adding a substance having the same trapping moiety with the functional group. When the functional group is dinitrophenyl, for example, dinitrophenylamino acid such as dinitrophenyl lysine is used and when the functional group is biotinyl, biotin is used.

When the functional group binds to an antigen via —S—S— bond(s), a reagent capable of cleaving the —S—S— bond can release the modified antigen-antibody complex.

The receptor substance to be adhered to a well type solid phase is a receptor substance B which re-traps immune complex at the moiety other than the moiety concerned with the earlier trapping. That is, a substance which specifically binds directly to an antibody in the immune complex (namely, antibody to be assayed) or a substance having a reactive group capable of specifically binding to the functional group previously introduced onto the antigen. Note that this functional group does not react with the receptor substance A.

The substance which specifically binds directly to an antibody is typically an antibody against said antibody, i.e. anti-antibody antibody.

The functional group previously introduced onto the antigen is a substance different from the functional group which reacts with the receptor substance A and is selected from the group consisting of haptens such as dinitrophenyl group, mononitrophenyl group, trinitrophenyl group and fluorescein group, and biotin. Accordingly, the substance having a reactive group capable of specifically binding to the functional group is anti-hapten antibody for hapten, avidin (streptoavidin) for biotin, and when sugar chain is present, it is, for example, lectin; protein A and immunoglobulin; hormone and hormone receptor; substrate or co-factor, and enzyme; or DNA. RNA and complementary DNA. RNA.

The receptor substance is adhered to a well type solid phase by a method similar to that for the above-mentioned dip stick type solid phase.

When a well type solid phase is used as the first solid phase and a dip stick type solid phase is used as the second solid phase, the receptor substances to be adhered to the surface of the both solid phases are exchanged.

When an antigen is to be assayed, the receptor substance is selected in the same manner as in the case where an antibody is assayed, and specific antibody, lectin and the like are used in the place of the antigen. Be it a dip stick type solid phase or a well type solid phase that is used as the first solid phase, the receptor substance to be adhered to the surface of the solid phase is a receptor substance A. When an antigen is to be assayed, the direction of transfer of the immune complex may be from a dip stick type solid phase to a well type solid phase, or vice versa. As in the case of antibody as the assay target, the receptor substances to be adhered to the surface of both solid phases are exchanged according to the direction of transfer.

The present invention is described in more detail in the following by way of Examples.

In Examples, antibodies were assayed by immune complex transfer immunoassay using the immunoassay plate of the present invention, and the assay sensitivity when the shortest distance between the immune complex binding surfaces is not more than 1 mm in 50% or more, or 50% or less of the area of the binding surface, was compared between the present invention and the conventional method using beads.

EXAMPLE 1

Using a dip stick type solid phase as the first solid phase and a well type solid phase as the second solid phase, an immune complex transfer immunoassay was performed. The direction of the transfer of the immune complex was from the dip stick type solid phase to the well type solid phase.

FIG. 5 schematically shows the outline of the steps and substances used in the instant Example. The respective substances (an antibody 20 to be assayed, an antigen 30 bound with a functional group 31, an antigen 40 bound with a label 41) constituting an immune complex 50, a receptor substance 3 (receptor substance A) adhered to the surface of the dip stick type solid phase 1, and a receptor substance 4 (receptor substance B) adhered to the surface of the well type solid phase 2 are as follows.

(1) Antibody 20 to be assayed

An antibody to be assayed was anti-human T cell leukemia virus-I antibody (abbreviated as anti-HTLV-I antibody) in serum. As the test serum, sera from healthy humans which tested positive or negative when tested using a gelatin particle coagulation kit (SERODIA-ATLA, Fujirebio, Tokyo, Japan) were used.

(2) Antigen 30 (same substance as antigen 40)

An antigen to be bound to the above-mentioned antibody 20 to constitute an immune complex was a peptide (abbreviated as Cys-env-gp46 (188–224)) prepared by ligating an N-terminal Cys at a site between 188th Pro to 224th Thr from the N-terminal of HTLV-I env-gp46 protein.

(3) Functional group 31

The functional group which binds to the above-mentioned antigen 30 to constitute an immune complex and which is involved in the trapping on the first solid phase was 2,4-dinitrophenyl-bovine serum albumin.

(4) Label 41

The label which binds to the above-mentioned antigen 40 to constitute an immune complex and which is used for assay was β-D-galactosidase.

(5) Receptor substance 3

As the receptor substance to be adhered to the dip stick type solid phase used as the first solid phase in the instant Example, rabbit anti-(2,4-dinitrophenyl-bovine serum albumin) antibody was used.

(6) Receptor substance 4

Rabbit anti-human IgG γ-chain antibody was used as the receptor substance to be adhered to the well type solid phase used as the second solid phase in the instant Example.

The outline of the steps of the immune complex transfer immunoassay of the instant Example is as follows.

(1) An antigen 30 and a functional group 31 are bonded. An antigen 40 and a label 41 are bonded. An immune complex 50 is formed.

(2) The immune complex 50 is trapped on a dip stick type solid phase and the solid phase is rinsed to leave only the immune complex 50. Trapping of the immune complex 50 is not necessarily conducted after the immune complex 50 has been formed. The functional group 31 may be trapped first and the immune complex 50 is formed with regard to the same, or these reactions may be mixed.

(3) The dip stick type solid phase is inserted into a transfer solution in a well type solid phase to release the immune complex 50, which is then trapped on the well type solid phase.

(4) The immune complex trapped on the well type solid phase is assayed by determining the label.

The preparation and purification of respective substances to be used for the immune complex transfer immunoassay, and detail of respective steps are described in the following.

Preparation of functional group 31

Thiol groups were introduced into bovine serum albumin (fraction V, Nacalai Tesque, Kyoto, Japan) using N-succinimidyl-S-acetylmercaptoacetate, and 2,4-dinitrophenyl groups were introduced by a known method [Kohono et al., J. Clin. Lab. Anal., ibid.] for reacting $\epsilon$ N-2,4-dinitrophenyl-L-lysine via N-succinimidyl-6-maleimidehexanoate. The number of the 2,4-dinitrophenyl groups introduced per one molecule of bovine serum albumin was 6.

Preparation of antigen 30-functional group 31 bond

By a known method [Kohono et al., J. Clin. Lab. Anal., Vol. 6, p 105 (1992)] comprising introducing maleimide into 2,4-dinitrophenyl-bovine serum albumin using N-succinimidyl-6-maleimidehexanoate and reacting same with Cys-env-gp46 (188–224) of HTLV-I, the bond was prepared.

Preparation of antigen 40-functional group 41 bond

By a known method (Kohono et al., J. Clin. Lab. Anal., ibid.) comprising introducing maleimide into β-D-galactosidase derived from *Escherichia coli* using N,N'-o-phenylenedimaleimide and reacting same with Cys-env-gp46 (188≧224) of HTLV-I, the bond was prepared.

Purification of receptor substance 3

By a known method [Ishikawa et al., J. Immunoassay, Vol. 4, p 209 (1983)] comprising subjecting a serum (Shibayagi, Gumma, Japan) containing rabbit anti-(2,4-dinitrophenyl-bovine serum albumin) antibody to salting out and ion exchange chromatography, rabbit anti-(2,4-dinitrophenyl-bovine serum albumin) antibody was purified.

Affinity purification of receptor substances 3 and 4

According to the manual of Pharmacia, 2,4-dinitrophenyl-bovine serum albumin and human IgG (10 mg) were made insoluble in CNBr-activated Sepharose 4B (1 g).

Then, rabbit anti-(2,4-dinitrophenyl-bovine serum albumin) antibody which is the receptor substance 3 and rabbit anti-human IgG γ-chain antibody which is the receptor substance 4 were affinity purified by a known method [Kohono et al., J. Biochem., Vol. 100, p 1247 (1986)] comprising elution at pH 2.5 using 2,4-dinitrophenyl-bovine serum albumin and human IgG-insoluble Sepharose 4B column.

Coating of receptor substance 3 on dip stick type solid phase 1

A 5 mm diameter column made from polystyrene, having a plane end perpendicular to the longitudinal axis thereof, was fixed at one end so that the other end thereof is located at 1 mm above the bottom of the well type solid phase when inserted in the well type solid phase in a combined manner.

The stick was washed with 10 g/L nonionic detergent SCAT20X-PF (Dai-Ichi Kogyo Seiyaku, Kyoto, Japan) and immersed in 0.1M sodium phosphate buffer, pH 7.0, containing 25 mg/L of rabbit anti-(2,4-dinitrophenyl-bovine serum albumin) antibody affinity-purified in the above, overnight at 4° C. to coat the receptor substance 3 on the entire surface up to 7.0 mm above the end of the stick by physical adsorption.

Said solid phase was preserved in 0.01M sodium phosphate buffer, pH 7.0, containing 0.1M sodium chloride, 1 mM magnesium chloride, 1 g/L bovine serum albumin and 1 g/L sodium azide at 4° C. until use.

Coating of receptor substance 4 on well type solid phase 2

0.1M Sodium phosphate buffer (pH 7.0, 280 μl) containing affinity-purified rabbit anti-human IgG γ-chain antibody (50 mg/L) was placed in a 6.6 mm inner diameter tubular well type solid phase having a plane bottom, and allowed to stand overnight at 4° C. to coat the receptor substance 4 on the entire surface up to 8.0 mm above the end by physical adsorption.

Said solid phase was washed with 0.01M sodium phosphate buffer, pH 7.0, containing 0.1M sodium chloride, 1mM magnesium chloride, 1 g/L bovine serum albumin and 1 g/L sodium azide. The same buffer (300 μl) was added and preserved at 4° C. until use.

Trapping of immune complex on dip stick type solid phase

As shown in FIG. 5(a), test serum, rabbit nonspecific serum, inactive β-D-galactosidase (β-galactosidase-Mutain, Behringer Mannheim AG, Germany), each 100 fmol of antigen 30-functional group 31 bond and antigen 40-label 41 bond were added in a well 6 having the same shape as the well type solid phase 2.

A dip stick type solid phase coated with the receptor substance 3 was inserted in this well, fixed so that the stick was dipped in the liquid up to 7.0 mm above the end, and left standing overnight at room temperature. As a result, an immune complex 50 was formed and trapped on the dip stick type solid phase.

This dip stick type solid phase was rinsed to leave only the trapped immune complex 50.

Transfer of immune complex from the first solid phase to the second solid phase

As shown in FIG. 5(b), 0.01M sodium phosphate buffer (pH 7.0, 150 μl) containing 1 mM $\epsilon$ N-2,4-dinitrophenyl-L-lysine, 0.1M sodium chloride, 1 mM magnesium chloride, 1 g/L bovine serum albumin and 1 g/L sodium azide was added in a well type solid phase 2 coated with the receptor substance 4. The dip stick type solid phase 1 on which the immune complex 50 had been trapped was inserted in this well type solid phase 2 in such a manner that the longitudinal axes thereof coincided. The solid phases were left standing at room temperature for one hour to liberate the immune complex. The dip stick type solid phase was pulled out, and the well type solid phase was left standing for 2 more hours. As a result, the immune complex 50 was trapped on the well type solid phase 2 via the antibody.

Measurement of antibody

The well type solid phase was washed twice with 300 μl of washing solution. Then, the solid phase was reacted for 1.5 hours according to a known method (Ishikawa et al., J. Immunoassay, ibid.) using 4-methylumbelliferyl-β-D-galactoside as a substrate, and the activity of β-D-galactosidase bound to the immune complex trapped on the surface of the well type solid phase was measured with a spectrofluorometer (RF-510, SHIMADZU CORPORATION, Kyoto, Japan).

The fluorescent intensity of respective positive test sample and negative test sample is shown in Table 1.

EXAMPLE 2

In the same manner as in Example 1 except that a well type solid phase was used as the first solid phase, a dip stick type solid phase was used as the second solid phase and the direction of the transfer of the immune complex was set in reverse from the well type solid phase to the dip stick type solid phase, an immune complex transfer immunoassay was performed.

The material and shape of the both solid phases, substances involved in reaction and preparation thereof were the same as in Example 1. Note, however, that the receptor substance adhered to the surface of the dip stick type solid phase by coating and the receptor substance adhered to the well type solid phase were reversed, namely, rabbit anti-human IgG γ-chain antibody was applied to the dip stick type solid phase and rabbit anti-(2,4-dinitrophenyl-bovine serum albumin) antibody was applied to the well type solid phase.

Trapping of immune complex on well type solid phase

Test serum, rabbit nonspecific serum, inactive β-D-galactosidase, each 100 fmol of antigen-functional group bond and antigen-label bond were added in a well type solid phase, and the solid phase was left standing overnight at room temperature. As a result, an immune complex 50 was formed and trapped on the well type solid phase.

This well type solid phase was rinsed to leave only the trapped immune complex 50.

Transfer of immune complex from the first solid phase to the second solid phase 0.01M Sodium phosphate buffer (pH 7.0, 150 $\mu$l) containing 1 mM ε N-2,4-dinitrophenyl-L-lysine, 0.1M sodium chloride, 1 mM magnesium chloride, 1 g/L bovine serum albumin and 1 g/L sodium azide was added in this well type solid phase to liberate the immune complex.

A dip stick type solid phase coated with a receptor substance was inserted in this well type solid phase, and the well type solid phase was left standing at room temperature for 3 hours. As a result, the immune complex was trapped on the dip stick type solid phase via the antibody.

Measurement of antibody

The dip stick type solid phase was washed with a washing solution. Then, the solid phase was inserted into a black microplate (protein nonadsorbing, Dainippon Pharmaceutical Co., Ltd., Osaka, Japan) and the activity of β-D-galactosidase bound to the immune complex trapped on the surface of the dip stick type solid phase was measured in the same manner as in Example 1 using a spectrofluorometer.

The fluorescent intensity of respective positive test sample and negative test sample is shown in Table 1.

EXAMPLE 3

The sensitivity of the assay of Example 1 was examined when the shortest distance between the immune complex binding surface of the dip stick type solid phase and that of the well type solid phase was mostly beyond 1 mm.

This Example is the same as Example 1 except the following two points.

(1) The shape of the dip stick type solid phase was as shown in FIG. 2(c) wherein the tip of the column is spherical. A receptor substance was coated on the surface of the spherical portion to use same as an immune complex binding surface.

(2) The shortest distance between the immune complex binding surfaces of the dip stick type solid phase and the well type solid phase was mostly set to beyond 1 mm.

The dip stick type solid phase was made from polystyrene and the spherical portion was 5 mm in diameter and the columnar portion was 3 mm in diameter. The inner size of the well type solid phase was 6.6 mm in diameter. The distance between the bottom surface of the well type solid phase and the top end of the dip stick type solid phase was 1.0 mm when the dip stick type solid phase was inserted into the well type solid phase.

Measurement of antibody

In the same manner as in Example 1, the antibody was determined by immune complex transfer immunoassay when the transfer direction of the immune complex was from the dip stick type solid phase to the well type solid phase. The fluorescent intensity was measured on a fluorescent microplate reader (Fluoroskan II, Labsystems, Finland).

The fluorescent intensity of respective positive test sample and negative test sample is shown in Table 1.

EXAMPLE 4

The assay sensitivity and signal amount in the assay of Example 2 were examined when the shortest distance between the immune complex binding surface of the dip stick type solid phase and that of the well type solid phase was mostly greater than 1 mm.

The material and shape of the dip stick type solid phase and the well type solid phase were the same as in Example 3.

Measurement of antibody

In the same manner as in Example 2, the antibody was determined by immune complex transfer immunoassay when the direction of the transfer of the immune complex was from the well type solid phase to the dip stick type solid phase.

The fluorescent intensity of respective positive test sample and negative test sample is shown in Table 1.

Comparative Example 1

The sensitivity and handling property of the conventional immune complex transfer immunoassay were examined using spherical beads as the first solid phase and the second solid phase. The respective substances involved in reaction and preparation thereof are the same as in Example 1.

The beads for the first solid phase were blue and those for the second solid phase were white. The beads were 3.2 mm in diameter, spherical, and were made from polystyrene (Immuno Chemical, Okayama, Japan).

The receptor substances were coated on the beads in the same manner as in Example 1. The first solid phase beads were applied with rabbit anti-(2,4-dinitrophenyl-bovine serum albumin) antibody and the second solid phase beads were applied with rabbit anti-human IgG γ-chain antibody.

Trapping of immune complex on first solid phase beads

Test serum, rabbit nonspecific serum, inactive β-D-galactosidase, antigen-functional group bond and antigen-label bond were added in a test tube. Two first solid phase beads were placed in this test tube with tweezers, and the test tube was left standing overnight at room temperature. As a result, an immune complex was formed and trapped on the first solid phase beads.

The two first solid phase beads were rinsed to leave only the trapped immune complex.

Transfer of immune complex from the first solid phase to the second solid phase

The two first solid phase beads and two second solid phase beads were inserted, with tweezers, into a different test tube containing 0.01M sodium phosphate buffer (pH 7.0, 170 μl) supplemented with 1 mM ε N-2,4-dinitrophenyl-L-lysine, 0.1M sodium chloride, 1 mM magnesium chloride, 1 g/L bovine serum albumin and 1 g/L sodium azide, and the test tube was incubated for one hour. Then, the two first solid phase beads were removed with tweezers, and the test tube was incubated for two more hours. As a result, the immune complex was liberated from the first solid phase beads and trapped on the second solid phase beads via the antibody.

Measurement of antibody

The second solid phase beads were washed twice with 2 ml of washing solution. Then, the two beads were transferred to a different test tube with tweezers and the activity of β-D-galactosidase bound to the immune complex trapped on the surface of the second solid phase beads was measured in the same manner as in Example 1 using a spectrofluorometer (RF-510, SHIMADZU CORPORATION, Kyoto, Japan).

The fluorescent intensity of respective positive test sample and negative test sample is shown in Table 1.

TABLE 1

|  | Fluorescent intensity | | Sensitivity |
| --- | --- | --- | --- |
|  | negative serum | positive serum | positive/negative |
| Example 1 | 5.67 | 372 | 64.6 |
| Example 2 | 9.67 | 502 | 51.9 |
| Example 3 | 0.48 | 16.1 | 33.5 |
| Example 4 | 0.71 | 19.0 | 26.8 |
| Comp. Ex. 1 | 4.03 | 183 | 45.4 |

Examples 1–4 and Comparative Example 1 revealed the following two points.

(1) Simplification of steps and operation

Examples 1–4 were free of handling with tweezers, washing and discerning of beads, and the immune complex transfer immunoassay was extremely easily performed as compared with Comparative Example 1 using beads.

(2) Different assay sensitivity according to the distance between solid phases

Comparison of the results of Examples 1 and 2, and the results of Examples 3 and 4 as shown in Table 1 readily reveals an improved sensitivity achieved by setting the distance between the binding surfaces of the solid phases to not more than 1 mm in 50% or more of the binding surfaces rather than setting same to greater than 1 mm. Thus, the importance of the close location of the solid phases to each other in immune complex transfer immunoassay was confirmed.

EXAMPLE 5

Anti-HTLV-I antibody was assayed using the dip stick type solid phase and the well type solid phase as shown in FIG. 7 in combination. The same immune complex transfer immunoassay as in Example 1 was performed except the following steps.

Coating of receptor substance 3 on dip stick type solid phase 1

A dip stick type solid phase as shown in FIG. 7 was inserted into the well of an ordinary microplate (Farcon 3072, Becton Dickinson, Calif., USA) containing 0.1M sodium phosphate buffer (pH 7.0, 150 μl) supplemented with 3 μg/ml affinity-purified rabbit anti-(2,4-dinitrophenyl-bovine serum albumin) antibody and 0.1% sodium azide, and the microplate was left standing overnight. The solid phase was immersed in an ordinary microplate well containing 0.01M sodium phosphate buffer (pH 7.0, 200 μl) supplemented with 0.1M sodium chloride, 1 mM magnesium chloride, 0.1% bovine serum albumin and 0.1% sodium azide, and preserved until use.

Coating of receptor substance 4 on well type solid phase 2

0.1M Sodium phosphate buffer (pH 7.0, 280 μl) containing 5 μg/ml affinity-purified rabbit anti-human IgG γ-chain antibody and 0.1% sodium azide was added in the wells of a black microplate (H type, Sumitomo Bakelite, Tokyo, Japan), and the microplate was left standing overnight. The solid phase was added with 0.01M sodium phosphate buffer (pH 7.0, 400 μl) containing 0.1M sodium chloride, 1 mM magnesium chloride, 0.1% bovine serum albumin and 0.1% sodium azide, and preserved until use.

Trapping of immune complex on dip stick type solid phase

Test serum, rabbit nonspecific serum, inactive β-D-galactosidase, each 100 fmol of antigen 30-functional group 31 bond and antigen 40-label 41 bond were added in the wells of an ordinary microplate (total amount 150 μl) as in Example 1. The plate was incubated for 30 minutes. A dip stick type solid phase on which a receptor substance 3 was coated was inserted therein and incubated for 2 hours. As a result, an immune complex 50 was formed and trapped on the dip stick type solid phase.

The dip stick type solid phase was rinsed to leave only the trapped immune complex 50.

Transfer of immune complex from the first solid phase to the second solid phase

A solution (150 μl) containing 1 mM ε N-2,4-dinitrophenyl-L-lysine was added to a well type solid phase 2 coated with the receptor substance 4, and the dip stick type solid phase 1 on which the immune complex 50 had been trapped was inserted therein, followed by incubation for 2 hours. As a result, the immune complex 50 was trapped on the well type solid phase 2 via the antibody.

Measurement of antibody

The well type solid phase was washed and reacted for one hour using 4-methylumbelliferyl-β-D-galactoside as a substrate. After the reaction, 0.1M glycine-sodium hydroxide buffer, pH 10.3, 50 μl, and 3 μl of 8M sodium hydroxide were added and the mixture was left standing for about 15 minutes. The fluorescent intensity was measured on a fluorescent microplate reader as in Examples 3 and 4.

Every step mentioned above was done at room temperature.

The fluorescent intensity of respective positive test sample and negative test sample is shown in Table 2.

Comparative Example 2

The same test as in Comparative Example 1 was performed except that the reaction conditions of each step such as incubation time were the same as in Example 5.

The fluorescent intensity of respective positive test sample and negative test sample is shown in Table 2.

TABLE 2

|  | Fluorescent intensity | | Sensitivity |
| --- | --- | --- | --- |
|  | negative serum | positive serum | positive/negative |
| Example 5 | 0.40 | 35.9 | 89.5 |
| Comp. Ex. 2 | 3.80 | 272 | 71.6 |

A combination of a dip stick type solid phase coated with a receptor substance and a well type solid phase coated with a receptor substance as the two kinds of solid phases used in immune complex transfer immunoassay results in markedly simplified operation of the steps, as compared with the conventional methods using two kinds of beads. In addition, by reducing the distance between the two solid phases to not more than 1 mm, transfer efficiency was improved and the assay became highly sensitive.

A constriction or a protrusion formed as described in the foregoing specification on the dip stick type solid phase allows easier and more accurate immune complex transfer immunoassay.

What is claimed is:

1. An immunoassay plate for use in an immune complex transfer immunoassay, comprising 2 solid phases, a coated well and an insertable, coated dip stick, wherein one of the two phases is coated with a receptor substance
(A) having a reactive group which specifically binds to a functional group previously introduced onto a substance which specifically forms an immune complex with a test substance and the other phase is coated with a receptor substance (B) having a reactive group which specifically binds to the following (i), (ii) or (iii):
(i) the test substance,
(ii) a substance which specifically forms an immune complex with the test substance, or
(iii) a functional group previously introduced on to the substance which specifically forms an immune complex with the test substance,
provided that the functional group which binds to the reactive group of (A) does not bind to the reactive group of (B) and vice versa.

2. An immunoassay plate for use in an immune complex transfer immunoassay, comprising 2 solid phases, a coated well and an insertable, coated dip stick, wherein one of the two phases is coated with a receptor substance (A) having a reactive group which specifically binds to a functional group previously introduced onto an antigen against a specific antibody to be assayed and the other phase is coated with a receptor substance (B) having a reactive group which specifically binds to the following (i), (ii) or (iii):
(i) the specific antibody to be assayed,
(ii) an antigen against the specific antibody to be assayed, or
(iii) a functional group previously introduced onto the antigen against the specific antibody to be assayed, provided that the functional group binds to the reactive group of (A) does not bind to the reactive group of (B) and vice versa.

3. The immunoassay plate of claim 1 or claim 2 wherein the distance between the dip stick and the well, when the two phases are combined by inserting the dip stick into the well, is not more than 1 mm for 50% of an immune complex binding surface of the dip stick.

4. The immunoassay plate of claims 1 or 2, wherein the dip stick, the well or a combination thereof is applied with a surface treatment to increase the amount of absorbed protein.

5. The immunoassay plate of claim 1 wherein the dip stick, the well or a combination thereof comprises polystyrene.

6. The immunoassay plate of claim 1, wherein the functional group which is introduced onto the substance which specifically forms the immune complex with the test substance and binds to the substance (A) is a hapten, and the substance (A) is an anti-hapten antibody, which is antidinitrophenyl antibody, anti-mononitrophenyl antibody or anti-trinitrophenyl antibody.

7. The immunoassay plate of claim 1 wherein the dip stick has an immune complex binding surface which is columnar in shape and has a conical pointed end.

8. The immunoassay plate of claim 1 wherein the dip stick has a constriction.

9. The immunoassay plate of claim 8, wherein the constriction is tapered.

10. The immunoassay plate of claims 1 to 8 wherein at least one of the dip stick or the well where an immune complex binding surface has been formed has one or more protrusions having a height of not more than 1 mm formed on the immune complex binding surface thereof, and the dip stick is columnar in shape.

11. The immunoassay plate of claim 10, wherein the protrusion on the dip stick protrudes toward a peripheral direction ay from the immune complex binding surface and has a ridge line extending along the longitudinal direction of the immune complex binding surface.

12. The immunoassay plate of claim 10, wherein protrusions are formed on both the dip stick and the well.

13. The immunoassay plate of claims 1 to 10, having a plurality of wells set in a predetermined arrangement on a plate which correspond to a plurality of dip sticks set on a different plate in the same arrangement.

14. An immunoassay assembly comprising:
(1) a first immunoassay plate on which are arranged at least three coated wells; and
(2) a second immunoassay plate on which are set at least three coated, insertable dip sticks in a corresponding arrangement to the wells, provided that each dip stick comprises a protrusion,
wherein the well or the dip stick is coated with a receptor substance (A) having a reactive group which specifically binds to a functional group previously introduced onto a substance which specifically forms an immune complex with a test substance and the other phase is coated with a receptor substance (B) having a reactive group which specifically binds to the following (i), (ii) or (iii):
(i) the test substance,
(ii) a substance which specifically forms an immune complex with the test substance, or
(iii) a functional group previously introduced onto the substance which specifically forms an immune complex with the test substance, provided that the functional group which binds to the reactive group of (A) does not bind to the reactive group of (B) and vice versa.

15. An immunoassay assembly according to claim 14, comprising at least three protrusions disposed on the dip sticks, wherein contact between the wells and the dip sticks is prevented.

16. The immunoassay assembly of claim 14 comprising, on the dip stick four protrusions that are equidistant.

17. An immune complex transfer immunoassay comprising the steps of:
(A) reacting, in a test sample solution, a test substance and a substance which specifically forms an immune complex with the test substance;
(B) trapping the immune complex in the test sample solution on an immune complex binding surface of a dip stick which has been coated with a receptor substance having a reactive group which specifically binds to a functional group previously introduced onto a substance which specifically forms an immune complex with the test substance,
(C) releasing, from said dip stick, the immune complex into a liquid phase in the well (D) trapping the immune complex on an immune complex binding surface of the well which has been coated with a receptor substance having a reactive group which specifically binds to the following (I), (ii) or (iii):
   (I) the test substance,
   (ii) the substance which specifically forms an immune complex with the test substance,
   (iii) a functional group previously introduced onto the substance which specifically forms an immune complex with the test substance,
   provided that the functional group which binds to the reactive group of (A) does not bind to the reactive group of (B) and vice versa; and
(E) assaying the immune complex trapped on said well.

18. An immune complex transfer immunoassay comprising the steps of:
   (A) reacting, in a test sample solution, a test substance and a substance which specifically forms an immune complex with the test substance,
   (B) trapping the immune complex in the test sample solution on an immune complex binding surface of a well which has been coated with a receptor substance having a reactive group which specifically binds to a functional group previously introduced onto a substance which specifically forms an immune complex with the test substance,
   (C) releasing, from said well, the immune complex into a liquid phase in the well;
   (D) trapping the immune complex on an immune complex binding surface of a dip stick coated with a receptor substance having a reactive group which specifically binds to the following (i), (ii) or (iii):
      (i) the test substance,
      (ii) the substance which specifically forms an immune complex with the test substance,
      (iii) a functional group previously introduced onto the substance which specifically forms an immune complex with the test substance,
      provided that the functional group which binds to the reactive group of (A) does not bind to the reactive group of (B) and vice versa; and
   (E) assaying the immune complex trapped on said dip stick.

19. The immune complex transfer immunoassay of claim 17, wherein, in steps (C) and (D), the distance between the immune complex binding surface of the dip stick and that of the well is not more than 1 mm.

20. The immune complex transfer immunoassay of claim 18, wherein, in steps (C) and (D), the distance between the immune complex binding surface of the dip stick and that of the well is not more than 1 mm.

* * * * *